US006783534B2

(12) United States Patent
Mehdizadeh

(10) Patent No.: US 6,783,534 B2
(45) Date of Patent: Aug. 31, 2004

(54) BONE WAX APPLICATOR

(76) Inventor: Hamid M. Mehdizadeh, 14928 Diduca Way, Los Gatos, CA (US) 95032

( * ) Notice: Subject to any disclaimer, the term of this patent is extended or adjusted under 35 U.S.C. 154(b) by 171 days.

(21) Appl. No.: 10/207,669

(22) Filed: Jul. 29, 2002

(65) Prior Publication Data

US 2004/0019355 A1 Jan. 29, 2004

(51) Int. Cl.$^7$ ............................................. A61B 17/56
(52) U.S. Cl. ........................................................ 606/93
(58) Field of Search .................. 606/92–95; 604/59–64, 604/207, 208; 222/391, 325–327, 390

(56) References Cited

U.S. PATENT DOCUMENTS

| | | | | | |
|---|---|---|---|---|---|
| 1,729,219 A | * | 9/1929 | Kellogg | .................. | 222/326 |
| 1,965,691 A | * | 7/1934 | Creveling | .................. | 222/259 |
| 3,640,431 A | * | 2/1972 | Plumer | .................. | 222/48 |
| RE28,120 E | * | 8/1974 | Plumer | .................. | 222/326 |
| 4,338,925 A | * | 7/1982 | Miller | .................. | 606/94 |
| 4,421,433 A | * | 12/1983 | Villanueva | .................. | 401/175 |
| 4,546,767 A | * | 10/1985 | Smith | .................. | 606/93 |
| 4,998,645 A | * | 3/1991 | Pearson | .................. | 222/98 |
| 5,108,403 A | * | 4/1992 | Stern | .................. | 606/93 |
| 5,431,654 A | * | 7/1995 | Nic | .................. | 606/92 |
| 6,086,594 A | * | 7/2000 | Brown | .................. | 606/92 |

* cited by examiner

*Primary Examiner*—Michael B. Priddy
(74) *Attorney, Agent, or Firm*—Henry M. Stanley

(57) ABSTRACT

A bone wax applicator has a cylinder magazine for storing bone wax and a piston for movement within the cylinder in response to manual activation of a trigger connected to the piston. The wax is moved out of the cylinder magazine through a tube mounted to communicate with one end of the cylinder magazine. The tube has a free end extending from the cylinder magazine with an opening at the free end. A dissector tip is attached to the free end adjacent the opening. Wax exuded from the opening is available to be spread on bleeding bone surfaces using the dissector tip.

12 Claims, 2 Drawing Sheets

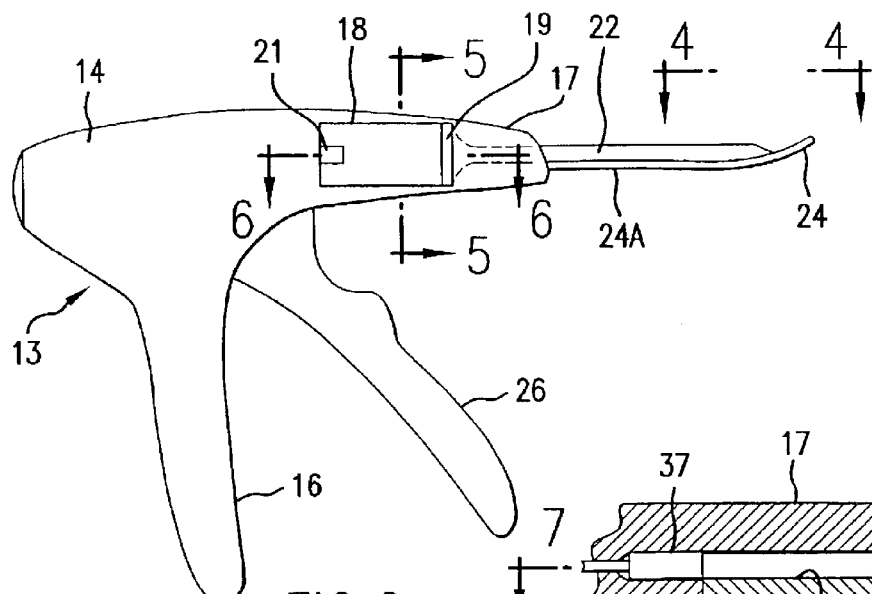
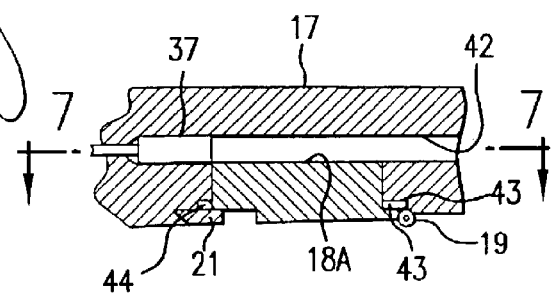
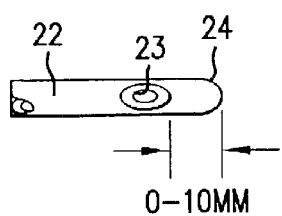
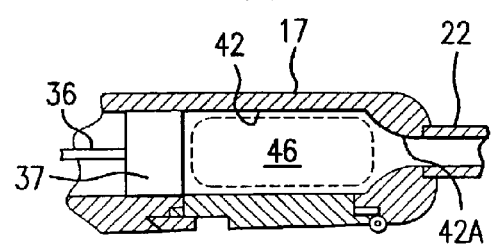
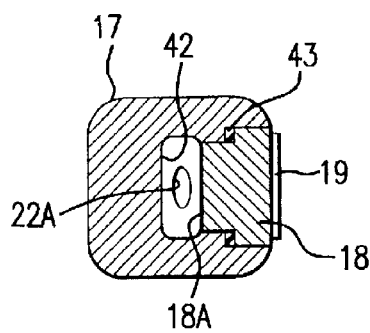
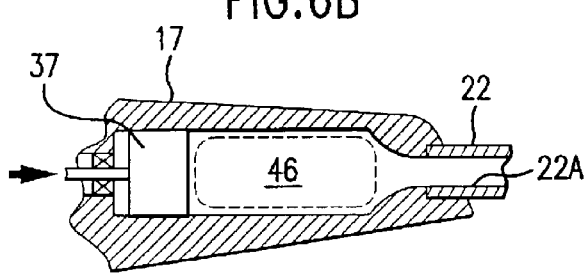

BONE WAX APPLICATOR

BACKGROUND OF THE INVENTION

When bone is cut or opened, the bone bleeds. During surgical procedures, if it is necessary to cut or open a section of bone, bone wax is applied along the cut or open section to stem the bleeding. In the past the bone wax applicator has taken the form of the dissector 10 shown in FIG. 1 of the drawings. The dissector of FIG. 1 is known as a "Penfield" and has a manually engageable handle 11 and a flattened tip 12 formed at an angle to the handle. The flattened tip is used to apply and spread the bone wax over the cut or open section of bone. The dissector tip 12 comes in varying sizes and is selectable by the surgeon to accommodate the task at hand. The "Penfield" tip is shaped somewhat in the form of a spatula and the present invention envisions size variations of the tip to accommodate the surgeon's preference.

SUMMARY OF THE INVENTION

A bone wax applicator has means for providing a force and contains a cylinder having a piston end and an outlet end. A piston is coupled to the force and is disposed within the cylinder for close sliding fit therein and for movement between the cylinder piston end and the cylinder outlet end in response to application of the force. The cylinder has an access opening and an access opening cover that is moveable between open and closed positions. An open wax transport tube is connected at one end to the cylinder outlet end and has an opposing free end. The opposing free end has a discharge opening. A dissector tip is attached to the opposing free end adjacent the discharge opening.

A bone wax applicator is useful for controlling bone bleeding, wherein the applicator contains a manually engageable force generator and a cylinder having an axial length, a piston end and an outlet end. A piston is connected to the manually engageable force generator. The piston is configured for close sliding fit within the cylinder and for movement between the cylinder piston and cylinder outlet ends. The cylinder has an accessible wax receiving chamber therein when the piston is positioned at the piston end of the cylinder. An access cover is provided for the wax receiving chamber, wherein the access cover is moveable between open and closed positions. A wax distribution tube is connected at one end to the cylinder outlet end and has a wax outlet port at an opposing free end. A dissector tip is mounted adjacent the wax outlet port for applying the wax supplied through the wax outlet port.

A bone wax application gun has a gun body with a gun handle depending from the gun body. A gun barrel extends laterally from the gun body. A gun trigger is pivotally mounted in the gun body and has an accessible free end and an opposing end. A cylinder having an axial length and an outlet end is mounted in the gun barrel. A piston is configured for a close sliding fit within the chamber. Means for providing movement of the piston along the cylinder axial length is disposed between the gun trigger opposing end and the piston, wherein such means is responsive to gun trigger pivotal motion. A wax transport tube is attached at one end to the cylinder outlet end and extends toward a free end from the gun barrel. The wax transport tube has a hole in the free end and a dissector tip is mounted on the wax transport tube adjacent to the free end. The cylinder has an accessible wax containment chamber therein.

BRIEF DESCRIPTION OF THE DRAWINGS

FIG. 1 is an elevation of an existing dissector used to apply wax to exposed bone interior.

FIG. 2 is an elevation of one embodiment of the bone wax applicator of the present invention.

FIG. 4 is a detail taken along the line 4—4 of FIG. 2.

FIG. 5 is a section taken along the line 5—5 of FIG. 2.

FIG. 6A is a section of one embodiment of the present invention taken along the line 6—6 of FIG. 2.

FIG. 6B is a section of an alternative embodiment of the present invention taken along the line 6—6 of FIG. 2.

FIG. 7 is a section taken along the line 7—7 of FIG. 6A.

DESCRIPTION OF THE PREFERRED EMBODIMENTS

Figure 3:
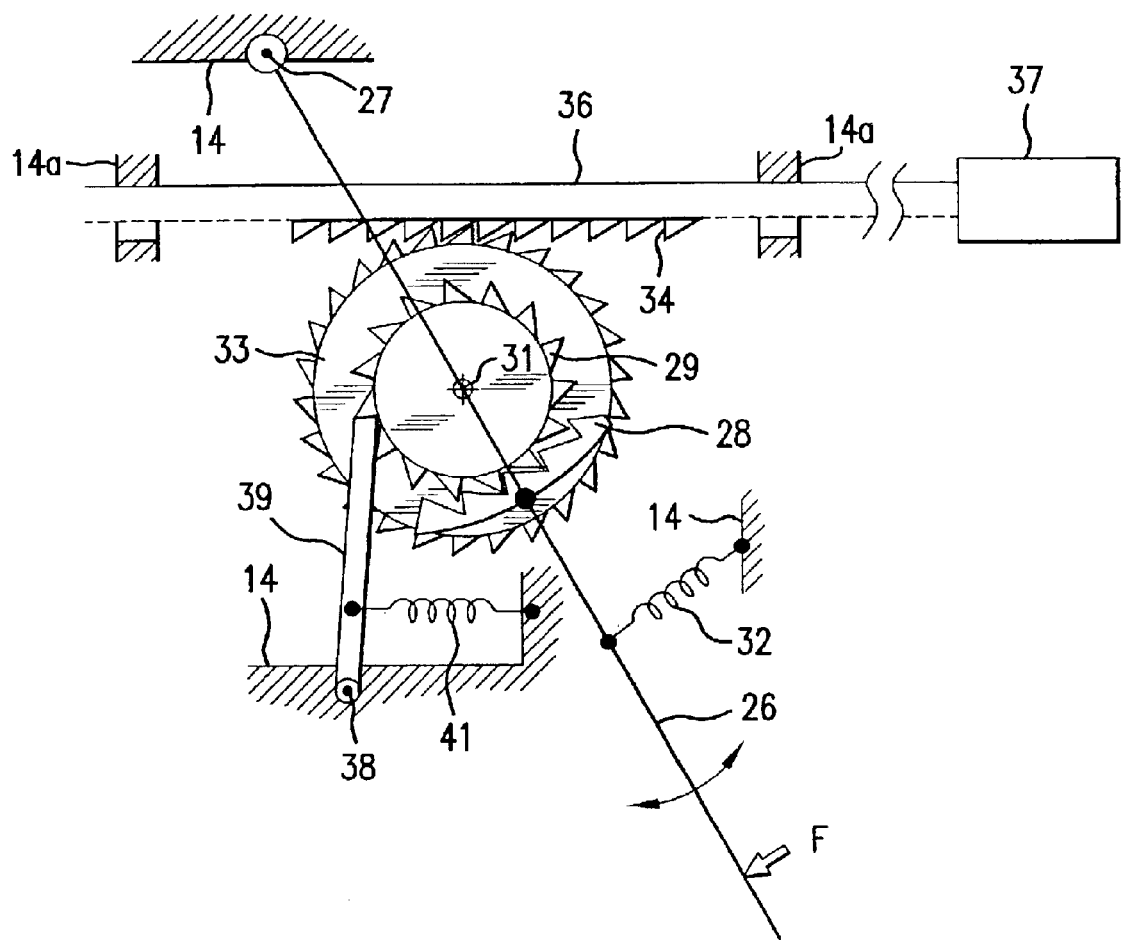
FIG. 3 is a schematic depiction of a portion of the internal mechanism of the embodiment of FIG. 2.

One embodiment of the present invention takes the form of the gun-like device depicted at 13 in FIG. 2 of the drawings. The gun-like form has been used for surgical tools for different purposes than that envisioned for the invention disclosed herein; i.e., disposable skin stapler, Auto Suture (tm) made by Multifire, Inc. The gun-like form 13 of FIG. 2 has gun body portion 14 from which depends a gun handle 16. A barrel portion 17 extends laterally from the gun body having a door or access closure 18 located on the barrel portion. The door has a hinge 19 and a latch 21, so that the door may be opened or closed from the barrel portion 18 and may be latched in the closed position by the latch 21. A hollow wax distribution tube 22 extends from the free end of the barrel 17. The wax distribution tube has a free end cut somewhat on a bias as seen in FIG. 2, so that a hole 23, best shown in FIG. 4, is formed at the free end of the tube 22. A tip 24, similar to the tip 12 of FIG. 1, is formed adjacent the hole 23, serving to collect bone wax extruded from the hole 23 for application to cut or open sections of bone by the tip. The tip 24 may have a body portion 24*a* extending back toward the free end of the barrel 17 for supporting the wax distribution tube 22. A trigger 26 is shown with a free end extending from the inside of the gun body 14 for a purpose to be hereinafter described. The tip 24, as previously discussed, is available in different sizes, for example, ranging from 2 through 5 millimeters in width. The inside diameter of tube 22 has been found to be conveniently about 3 millimeters. The extension of the tube 22 and the tip 24 from the free end of the barrel 17 has been established in a preferred embodiment as within the range of 7.5 to 10 centimeters.

The schematic showing of FIG. 3 includes structure represented as on the body 14 of the gun-like device 13, wherein the trigger 26 is pivotally attached to the gun body 14 at a pivot point 27. Forcing the trigger 26 to pivot about pivot 27 in the direction dictated by a force F in FIG. 3 causes a saw toothed rack 28 to rotate an inner saw toothed gear 29 in a clockwise direction. The gear 29 is fixed to and rotates with a shaft 31 mounted in the gun body as seen in FIG. 3. The rack 28 is therefore configured to rotate the inner gear 29 when the force F is applied and to resume a neutral position, as shown in FIG. 3, when the force F is removed. The trigger 26 is urged back into the neutral position by means such as the spring 32 extending between a position on the trigger 26 and a position on the body 14 of the gun-like device 13.

An outer saw toothed gear 33 is also mounted on the shaft 31 and therefore rotates in a clockwise direction with inner gear 29 when force F is applied to the trigger 26. Outer gear 33 has peripheral saw tooth shaped teeth thereon which engage saw tooth shaped teeth 34 formed on a piston rod 36, thereby driving the piston rod laterally to the right as seen in FIG. 3. A piston 37 is mounted on a free end of the piston rod 36 and the piston rod is supported by appropriate bearing means 14a within the gun body 14. The bone wax applicator of the invention described herein is a tool for operating room use and is therefore envisioned as a one-time use device. Therefore, an anti-reverse rotation lock arm 39 is pivoted about a point 38 on the gun body 14 and urged into engagement with the teeth on the inner gear 29 by a spring 41 to hold the piston 37 in the position to which it was advanced by application of the force F on the trigger 26. Alternatively, the anti-reverse rotation lock may be released by moving the lock arm 39 in a counterclockwise direction about pivot 38 if the purpose demands. It should be recognized that the structure represented in FIG. 3 of the drawings is merely a schematic depiction of the best known manner in which the piston 37 may be advanced within the cylinder 42. FIG. 3 may not represent the most efficient way in which to obtain the desired effect.

The section of FIG. 5 through a portion of the barrel 17 on the gun-like device shows the wall of an internal cylinder 42. The cylinder 42 is completed by the inside surface 18a on the door 18 previously described. An inside diameter 22a of the wax distribution tube 22 is also seen in FIG. 5. A seal 43 is provided between the door 18 and adjacent portions of the barrel 17 so that when the door 18 is closed and latched in the closed position, the cylinder formed by the walls 42 and 18a will not allow wax contained therein to escape past the door when the piston 37 is advanced within the cylinder.

In FIG. 6A, the cylinder formed by the cooperation of the walls 42 and the inner wall 18a of the door 18 is shown with the closely fitted piston 37 located therein. As previously described, the piston is advanced in a direction to the right in FIG. 6A by the application of force F on trigger 26 and the ratcheting action of the mechanism described in FIG. 3. The door hinge 19 and the seal 43 around the door are seen in FIG. 6A, together with the sliding latch 21 that enters a detent 44 when the door 18 is closed to retain the door in a closed position. It may be seen from FIG. 6A that when the door 18 is opened access is provided to the cylinder having the walls 42. In this fashion, a prepared flat wax patty is inserted within the cylinder 42 ahead of the piston 37. The wax used to facilitate stemming bone bleeding is beeswax and is prepared and packaged in sterile form.

With reference now to FIG. 6B of the drawings, it may be seen that the end of the cylinder formed by the walls 42 nearest the free end of the barrel portion 17 of the gun-like device has an opening 42a that is connected to one end of the wax distribution tube 22 and communicates with the inside diameter 22a of tube 22. A wax charge 46 is shown disposed within the cylinder 42 in the front of the piston 37. The cylinder and piston shapes of FIG. 6B are circular in cross section as opposed to the cross section of the cylinder shown in FIG. 5. Thus, in this embodiment, the wax charge 46 would be a volume in the shape of a circular cylinder. FIG. 6B is used to describe the outlet end 42a connected to the inside of the wax distribution tube 22 because there is more room in FIG. 6B to more clearly describe the interconnection with the tube 22. Nonetheless, the connection in the embodiment of FIG. 6A is the same as that described for the embodiment of FIG. 6B.

FIG. 7 depicts a section of the embodiment of FIG. 6A in elevation. As may be seen therein, the wax patty 46 is placed within the cylinder formed by the cylinder walls 42 in a position ahead of the piston 37, so that the wax may be advanced through the inside diameter of the wax distribution tube as the force F advances the piston 37 along the axial length of the cylinder 42.

Although the best mode contemplated for carrying out the present invention has been shown and described herein, it will be understood that modification and variation may be made without departing from what is regarded to be the subject matter of the invention.

What is claimed:

1. A bone wax applicator, comprising
   means for providing a force,
   a cylinder having a piston end and an outlet end,
   a piston coupled to said means for providing a force and disposed within said cylinder for close sliding fit therein and for movement between said cylinder piston end and said cylinder outlet end in response to said force,
   said cylinder having an access opening,
   an access opening cover moveable between open and closed positions,
   an open wax transport tube connected at one end to said cylinder outlet end and having an opposing free end,
   said opposing free end having a discharge opening, and
   a dissector tip attached to said opposing free end adjacent said discharge opening.

2. The bone wax applicator of claim 1, wherein said means for providing a force comprises
   a manually engageable lever coupled to said piston.

3. The bone wax applicator of claim 1, comprising
   a seal between said access opening cover and said access opening.

4. The bone wax applicator of claim 1, wherein said cylinder has an elongate cross section.

5. The bone wax applicator of claim 1, wherein said cylinder has a circular cross section.

6. A bone wax applicator for controlling bone bleeding, comprising
   a manually engageable force generator,
   a cylinder having an axial length, a piston end and an outlet end,
   a piston connected to said manually engageable force generator, said piston being configured for close sliding fit within said cylinder and for movement between said cylinder piston and cylinder outlet ends,
   said cylinder having an accessible wax receiving chamber therein when said piston is positioned at said piston end,
   an access cover for said wax receiving chamber moveable between open and closed positions,
   means for providing a seal between said accessible wax receiving chamber and said access cover in said closed position,
   a wax distribution tube connected at one end to said cylinder outlet end and having a wax outlet port at an opposing free end, and
   a dissector tip mounted adjacent said wax outlet port for applying wax supplied through said wax outlet port.

7. The bone wax applicator of claim 6, wherein said manually engageable force generator comprises
   a pivoting trigger member having an engageable free end and an opposing end connected to said piston.

8. The bone wax applicator of claim 6, wherein said cylinder has an elongate cross section.

9. The bone wax applicator of claim 6, wherein said cylinder has a circular cross section.

10. A bone wax application gun, comprising
    a gun body,
    a gun handle depending from said gun body,
    a gun barrel extending laterally from said gun body, a gun trigger pivotally mounted in said gun body, having an accessible free end and an opposing end, a cylinder having an axial length and an outlet end mounted in said gun barrel, a piston configured for a close sliding fit within said cylinder, means responsive to gun trigger pivotal motion disposed between said gun trigger opposing end and said piston for providing movement of said piston along said cylinder axial length, a wax transport tube attached at one end to said cylinder outlet end and extending toward a free end from said gun barrel, said wax transport tube having a hole in said free end, and a dissector tip mounted on said wax transport tube adjacent said free end, said cylinder having an accessible wax containment chamber therein, said accessible wax containment chamber having an opening therein, a chamber opening cover configured to fit within said opening and being movable between a closed and an open position, and a seal disposed between said containment chamber opening and said chamber opening cover when said cover is in said closed position.

11. The bone wax application gun of claim 10, wherein said cylinder is elongate in cross section.

12. The bone wax application gun of claim 10, wherein said cylinder is circular in cross section.

* * * * *